United States Patent
Nguyen-Kim et al.

(10) Patent No.: US 7,858,076 B2
(45) Date of Patent: Dec. 28, 2010

(54) COPOLYMERS BASED ON TERT-BUTYL(METH) ACRYLATE AND USE THEREOF

(75) Inventors: Son Nguyen-Kim, Hemsbach (DE); Claudia Wood, Weinheim (DE)

(73) Assignee: BASF SE, Ludwigshafen (DE)

( * ) Notice: Subject to any disclaimer, the term of this patent is extended or adjusted under 35 U.S.C. 154(b) by 1052 days.

(21) Appl. No.: 10/581,884

(22) PCT Filed: Dec. 8, 2004

(86) PCT No.: PCT/EP2004/013984

§ 371 (c)(1), (2), (4) Date: Jun. 6, 2006

(87) PCT Pub. No.: WO2005/058989

PCT Pub. Date: Jun. 30, 2005

(65) Prior Publication Data

US 2007/0116660 A1 May 24, 2007

(30) Foreign Application Priority Data

Dec. 9, 2003 (DE) ................................ 103 57 486

(51) Int. Cl.
*A61K 8/81* (2006.01)
*C08F 20/06* (2006.01)

(52) U.S. Cl. ............. 424/70.16; 526/317.1; 526/318.4; 526/328; 526/328.5

(58) Field of Classification Search ............. 424/70.16; 526/317.1, 318.4, 328, 328.5
See application file for complete search history.

(56) References Cited

U.S. PATENT DOCUMENTS

| 3,632,838 | A | 1/1972 | Wilhelm et al. |
| 3,927,199 | A | 12/1975 | Micchelli et al. |
| 4,748,989 | A | 6/1988 | Nuber et al. |
| 4,767,613 | A | 8/1988 | Nuber et al. |
| 5,025,062 | A | 6/1991 | Ley et al. |
| 5,110,582 | A | 5/1992 | Hungerbuhler et al. |
| 5,196,188 | A | 3/1993 | Potthoff-Karl et al. |
| 6,482,393 | B1 | 11/2002 | Schehlmann et al. |
| 7,015,294 | B2 * | 3/2006 | Dausch et al. ............. 526/319 |
| 2003/0147929 | A1 * | 8/2003 | Kim et al. ................... 424/401 |
| 2005/0265950 | A1 * | 12/2005 | Chrisstoffels et al. .... 424/70.17 |
| 2007/0141013 | A1 | 6/2007 | Nguyen-Kim et al. |

FOREIGN PATENT DOCUMENTS

| DE | 3227334 | 1/1984 |
| DE | 10331865 | 3/2005 |
| WO | WO2004058837 | 7/2004 |

* cited by examiner

*Primary Examiner*—David Wu
*Assistant Examiner*—Vu A Nguyen
(74) *Attorney, Agent, or Firm*—Connolly Bove Lodge & Hutz LLP

(57) ABSTRACT

Copolymers which contain tert-butyl (meth)acrylate, at least one α,β-ethylenically unsaturated amido-containing compound and acrylic acid incorporated in the form of polymerized units, cosmetic and pharmaceutical compositions which contain at least one such copolymer and the use of these copolymers are described.

8 Claims, No Drawings

COPOLYMERS BASED ON TERT-BUTYL(METH) ACRYLATE AND USE THEREOF

The present invention relates to copolymers which comprise tert-butyl (meth)acrylate, at least one α,β-ethylenically unsaturated amido-containing compound and acrylic acid incorporated in the form of polymerized units, cosmetic and pharmaceutical compositions which comprise at least one such copolymer and the use of these copolymers.

Polymers having film-forming properties have a variety of applications in pharmacy and cosmetics. In pharmacy, they serve, for example, as coating materials or binders for solid dosage forms. In cosmetics, polymers having film-forming properties are used, inter alia, for hair setting, for improving the structure of hair and for shaping the hair. They serve, for example, as conditioners for improving the dry and wet combability, the feel, the gloss and the appearance and for imparting antistatic properties to the hair. Requirements which film-forming polymers for use as setting resins have to meet are, for example, strong setting (also at high atmospheric humidity), elasticity, capability of being washed out from the hair, compatibility in the formulation and a pleasant handle of the hair treated therewith. The provision of products having a complex property profile often presents difficulties. Thus, there is a need for film-forming polymers for cosmetic hair compositions which are capable of forming substantially smooth, nontacky films, have a good setting effect and simultaneously impart good sensory properties, such as elasticity and a pleasant handle, to the hair. If these polymers are to be used in hair spray formulations, good propellant compatibility, suitability for use in low-VOC formulations (VOC=volatile organic compounds), good sprayability, good solubility in water or aqueous/alcoholic solvent mixtures and good washout properties are additionally desired.

It is known that polymers based on tert-butyl (meth)acrylate can be used in hair cosmetics. Thus, DE-A-32 27 334 (EP-A-0 100 890) describes copolymers which are obtainable by free radical copolymerization of a) at least one $C_2$-$C_{20}$-alkyl (meth)acrylate, e.g. tert-butyl (meth)acrylate, b) at least one water-soluble nitrogen-containing monomer, e.g. an N-vinyllactam, c) at least one monomer having cationic groups and d) at least one carboxylic acid capable of free radical polymerization.

DE-A-36 27 970 and DE-A40 31 912 describe terpolymers of vinylpyrrolidone, tert-butyl (meth)acrylate and acrylic acid or methacrylic acid and the use thereof in hair treatment compositions.

DE-A43 14 305 describes a hair setting composition which comprises, as a film former, a copolymer based on tert-butyl acrylate or tert-butyl methacrylate, acrylic acid or methacrylic acid and a monomer which is capable of free radical copolymerization and gives a homopolymer having a glass transition temperature of <30° C.

DE-A-100 08 263 describes a cosmetic composition which comprises at least one water-soluble or water-dispersible polymer which comprises, incorporated in the form of polymerized units, not more than 50% by weight of at least one tert-butyl ester and/or N-tert-butylamide of an α,β-ethylenically unsaturated carboxylic acid and at least one N-vinylamide and/or vinyllactam and at least one polymerizable compound having a cationogenic and/or cationic group.

WO 01/62809 describes a cosmetic composition which comprises at least one water-soluble or water-dispersible polymer which comprises incorporated
a) from 5 to 50% by weight of at least one α,β-ethylenically unsaturated monomer having a tert-butyl group,
b) from 25 to 90% by weight of at least one N-vinylamide and/or N-vinyllactam,
c) from 0.5 to 30% by weight of at least one compound having an α,β-ethylenically unsaturated double bond capable of free radical polymerization and at least one cationogenic and/or cationic group per molecule, and
d) from 0 to 30% by weight of at least one further α,β-ethylenically unsaturated compound, which may be a compound having at least one anionogenic and/or anionic group per molecule.

It is known that copolymers based on N-alkyl(meth)acrylamides can be used in cosmetic compositions. U.S. Pat. No. 3,927,199 describes a hair setting composition which comprises a film-forming binder resin based on a copolymer which comprises, incorporated in the form of polymerized units, 1) N-alkylacrylamides or methacrylamides, 2) monomers containing acid groups and 3) at least one further comonomer.

EP-A-0 062 002 describes a hair setting formulation which comprises a terpolymer of an N-alkyl(meth)acrylamide, a $C_1$-$C_4$-alkyl ester or a $C_1$-$C_4$-hydroxyalkyl ester of (meth) acrylic acid and acrylic acid or methacrylic acid. Terpolymers based on tert-butyl (meth)acrylate are not disclosed.

The unpublished German Patent Application P 102 61 750.3 describes an ampholytic copolymer which is obtainable by free radical copolymerization of
a) at least one ethylenically unsaturated compound having at least one anionogenic and/or anionic group,
b) at least one ethylenically unsaturated compound having at least one cationogenic and/or cationic group,
c) at least one unsaturated amido-containing compound and, if appropriate, further comonomers. Polyelectrolyte complexes which comprise such an ampholytic copolymer and cosmetic or pharmaceutical compositions based on these ampholytic copolymers and polyelectrolyte complexes are furthermore described.

The unpublished German Patent Application 102 37 378.7 describes the use of polymers which are obtainable by
(i) free radical copolymerization of monomer mixtures comprising
    (a) at least one cationic monomer or quaternizable monomer,
    (b) if appropriate, a water-soluble monomer,
    (c) if appropriate, a further monomer capable of free radical copolymerization,
    (d) at least one monomer acting as a crosslinking agent and having at least two ethylenically unsaturated, nonconjugated double bonds, and
    (e) at least one regulator,
(ii) subsequent quaternization or protonation of the polymer, provided that an unquaternized or only partly quaternized monomer is used as monomer (a), in cosmetic hair formulations.

The unpublished German Patent Application 103 31 865.8 describes an aqueous polymer dispersion Pd) which is obtainable by free radical polymerization of a monomer mixture M) comprising
a) at least one α,β-ethylenically unsaturated amido-containing compound of the formula I

where
R² is a group of the formula $CH_2=CR^4-$ and $R^1$ and $R^3$, independently of one another, are H, alkyl, cycloalkyl, heterocycloalkyl, aryl or hetaryl, or $R^1$ and $R^3$, together with the amido group to which they are bonded, are a lactam having 5 to 8 ring atoms, b) at least one crosslinking compound capable of free radical polymerization and having at least two α,β-ethylenically unsaturated double bonds per molecule, c) at least one compound having an α,β-ethylenically unsaturated double bond capable of free radical polymerization and at least one cationogenic and/or cationic group per molecule, in an aqueous medium in the presence of at least one polymeric anionic dispersant D). They are suitable as conditioners for cosmetic formulations, in particular shampoos.

The unpublished German Patent Application 102 37 378.7 describes a cosmetic or pharmaceutical composition which comprises at least one polyelectrolyte complex which comprises, as component A1), at least one water-soluble or water-dispersible copolymer having cationogenic groups, which comprises, incorporated in the form of polymerized units, vinylimidazole and/or a derivative thereof and at least one further monomer copolymerizable therewith, and, as component A2), at least one polymer containing acid groups.

In spite of extensive efforts, there is still a need for improvement in the case of the polymers known from the prior art and intended for the production of hair spray formulations having a low VOC value, good rheological properties and good sprayability in combination with strong setting (also at high atmospheric humidity).

Surprisingly, it has been found that copolymers which are obtainable by free radical polymerization of a monomer mixture comprising a) tert-butyl acrylate and/or tert-butyl methacrylate, b) at least one α,β-ethylenically unsaturated amido-containing compound of the formula I

(I)

where
$R^1$ is H or $C_1$-$C_4$-alkyl,
$R^2$ and $R^3$, independently of one another, are H or $C_1$-$C_4$-alkyl, or $R^2$ and $R^3$, together with the nitrogen atom to which they are bonded, may also be a 4- to 7-membered heterocycle,
with the proviso that the sum of carbon atoms of the radicals $R^1$, $R^2$ and $R^3$ is not more than 4, and c) acrylic acid, are particularly suitable for the abovementioned applications.

Below, compounds which may be derived from acrylic acid and methacrylic acid are in some cases abbreviated by adding the syllable "(meth)" in the compound derived from acrylic acid.

In the context of the present invention, water-soluble monomers and polymers are understood as meaning monomers and polymers which have a solubility of at least 1 g/l at 20° C. in water. Water-dispersible monomers and polymers are understood as meaning monomers and polymers which disintegrate into dispersible particles with application of shear forces, for example by stirring. Hydrophilic monomers are preferably water-soluble or at least one water-dispersible. The novel copolymers are generally water-soluble.

The novel copolymers are particularly advantageous for use in cosmetic compositions, in particular in hair treatment compositions. They preferably serve for producing elastic hairstyles in combination with strong setting. They advantageously also have both good propellant compatibility and good solubility in water or aqueous/alcoholic solvent mixtures. They can therefore be formulated both as hair sprays having a high propellant content (VOC at least 85% by weight) and as formulations having low VOC values (generally not more than 55% by weight, based on the total weight of the composition). The hair spray formulations in any case have very good sprayability.

For establishing certain product properties, a part of the monomers a) can be replaced by at least one monomer f). In a special embodiment, therefore, up to 50% by weight of the monomers of component a) can be replaced by at least one $C_1$-$C_3$-alkyl methacrylate and/or hydroxy-$C_1$-$C_3$-alkyl methacrylate. Suitable $C_1$-$C_3$-alkyl methacrylates and hydroxy-$C_1$-$C_3$-alkyl methacrylates are described below for component f). Ethyl methacrylate is preferably used.

Monomer a)

The novel copolymers comprise, as component a), tert-butyl acrylate and/or tert-butyl methacrylate incorporated in the form of polymerized units. Preferably, tert-butyl methacrylate is not used alone as component a). Copolymers in which the component a) comprises tert-butyl acrylate or consists thereof are therefore preferred.

The novel copolymers preferably comprise from 30 to 90, particularly preferably from 40 to 85, % by weight, based on the total weight of the monomers used for the polymerization, of at least one compound a) incorporated in the form of polymerized units.

Monomer b)

The copolymers comprise, as component b), at least one amide of an α, β-ethylenically unsaturated monocarboxylic acid of the formula I incorporated in the form of polymerized units. Preferably, the radicals $R^2$ and $R^3$ are both H or one of the radicals $R^2$ and $R^3$ is H and the other is $C_1$-$C_4$-alkyl in the compounds of the formula I.

Preferably, the amides of the formula I are derived from acrylic acid, methacrylic acid or ethacrylic acid as the α,β-ethylenically unsaturated monocarboxylic acid. Preferably, the component b) is selected from acrylamide, methacrylamide, N-methyl(meth)acrylamide, N-ethyl(meth)acrylamide, N-propyl(meth)acrylamide, N-(n-butyl)acrylamide, N-(sec-butyl)acrylamide, N-(tert-butyl)acrylamide, N,N-dimethyl(meth)acrylamide, N,N-diethylacrylamide, N-acryloylmorpholine, N-acryloylpiperazine, N-(meth)acryloylpyrrolidine and mixtures thereof.

Preferably, the component b) comprises methacrylamide and/or N-(tert-butyl)acrylamide or consists of one of these components or of a mixture of methacrylamide and N-(tert-butyl)acrylamide.

The novel copolymers preferably comprise from 3 to 50, particularly preferably from 5 to 40, in particular from 10 to 35, % by weight, based on the total weight of the monomers used for the polymerization, of at least one compound of the component b) incorporated in the form of polymerized units.

Monomer c)

The novel copolymers preferably comprise from 5 to 40, particularly preferably from 7 to 35, in particular from 10 to 30, % by weight, based on the total weight of the monomers used for polymerization, of acrylic acid (=monomer c)) incorporated in the form of polymerized units.

For the preparation of the copolymers, the acrylic acid c) can be used partly or completely in deprotonated form. The opposite ions thereof are then preferably derived from bases as described below for establishing the pH in the polymerization or of polymers obtained.

In a special embodiment, the novel copolymers consist only of monomer units of the abovementioned monomers a), b) and c). In further embodiments, the novel copolymers comprise additional monomers incorporated in the form of polymerized units. Suitable additional monomers are mentioned below.

Monomer d)

In a preferred embodiment, the copolymer additionally comprises methacrylic acid (=monomer d)) incorporated in the form of polymerized units. The copolymers then preferably comprise up to 25, particularly preferably up to 20, in particular up to 15, % by weight, based on the total weight of the monomers used for the polymerization, of methacrylic acid incorporated in the form of polymerized units. If methacrylic acid is used for the polymerization, it is preferably used in an amount of at least 1, particularly preferably at least 5, % by weight.

Monomer e)

The novel copolymers may additionally comprise, incorporated in the form of polymerized units, at least one compound having an α,β-ethylenically unsaturated double bond capable of free radical polymerization and at least one cationogenic and/or cationic group per molecule.

The cationogenic or cationic groups of the component e) are preferably nitrogen-containing groups, such as primary, secondary and tertiary amino groups and quaternary ammonium groups. The nitrogen-containing groups are preferably tertiary amino groups. The compounds e) are preferably used in uncharged form for the polymerization. However, use in charged form is also suitable. Charged cationic groups can be produced, for example from the amine nitrogens, by protonation, for example with monobasic or polybasic carboxylic acids, such as lactic acid or tartaric acid, or mineral acids, such as phosphoric acid, sulfuric acid and hydrochloric acid.

The component e) is preferably selected from esters of α,β-ethylenically unsaturated mono- and dicarboxylic acids with amino alcohols which may be mono- or dialkylated on the amine nitrogen, amides of α,β-ethylenically unsaturated mono- and dicarboxylic acids with diamines which have at least one primary or secondary amino group, N,N-diallylamine, N,N-diallyl-N-alkylamines and derivatives thereof, vinyl- and allyl-substituted nitrogen heterocycles, vinyl- and allyl-substituted heteroaromatic compounds and mixtures thereof.

Suitable compounds e) are the esters of α,β-ethylenically unsaturated mono- and dicarboxylic acids with amino alcohols. Preferred amino alcohols are $C_2$-$C_{12}$-amino alcohols which are $C_1$-$C_8$-mono- or -dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. Acrylic acid, methacrylic acid and mixtures thereof are preferably used. Particularly preferred compounds c2) are N-methylaminoethyl (meth)acrylate, N-ethylaminoethyl (meth)acrylate, N-(n-propyl)aminoethyl (meth)acrylate, N-(n-butyl)aminoethyl (meth)acrylate, N-(tert-butyl)aminoethyl (meth)acrylate, N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate and N,N-dimethylaminocyclohexyl (meth)acrylate. In particular, N-(tert-butyl)aminoethyl acrylate and N-(tert-butyl)aminoethyl methacrylate are used as compound e).

Suitable monomers e) are furthermore the amides of the abovementioned α,β-ethylenically unsaturated mono- and dicarboxylic acids with diamines which have at least one primary or secondary amino group. Preferred diamines are those which have a tertiary and a primary or secondary amino group. Preferably used monomers e) are N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide. N-[3-(dimethylamino)propyl]acrylamide and/or N-[3-(dimethylamino)propyl]methacrylamide are particularly preferably used.

Suitable monomers e) are furthermore N,N-diallylamines and N,N-diallyl-N-alkylamines and the acid addition salts thereof. Here, alkyl is preferably $C_1$-$C_{24}$-alkyl. For example, N,N-diallyl-N-methylamine is preferred.

Suitable monomers e) are furthermore vinyl- and allyl-substituted nitrogen heterocycles, such as N-vinylimidazole, N-vinylimidazole derivatives, e.g. N-vinyl-2-methylimidazole, vinyl- and allyl-substituted heteroaromatic compounds, such as 2- and 4-vinylpyridine, 2- and 4-allylpyridine, and the salts thereof.

Suitable monomers e) are also N-vinylimidazoles of the formula (I), where $R^1$ to $R^3$ are hydrogen, $C_1$-$C_4$-alkyl or phenyl

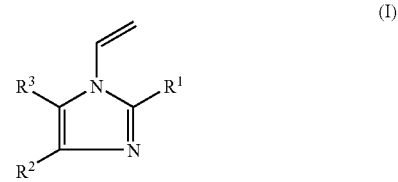

(I)

Examples of compounds of the formula (I) are shown in table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

The compounds of component e) are particularly preferably selected from N-(tert-butylamino)ethyl (meth)acrylate, N,N-dimethylaminoethyl (meth)acrylate, N-[3-(dimethylamino)propyl](meth)acrylamide, vinylimidazole and mixtures thereof.

The novel copolymers preferably comprise up to 25, particularly preferably up to 20, in particular up to 10, % by weight, based on the total weight of the monomers used for the polymerization, of at least one monomer e) incorporated in the form of polymerized units. If a monomer e) is used, it is preferably used in an amount of at least 1, particularly preferably at least 2, % by weight.

Monomer f)

The novel copolymers may additionally comprise, incorporated in the form of polymerized units, at least one monomer f) which differs from the components a) to e) and is copolymerizable therewith.

The component f) is preferably selected from esters of α,β-ethylenically unsaturated mono- and dicarboxylic acids with $C_1$-$C_{30}$-alkanols and $C_1$-$C_{30}$-alkanediols, which esters differ from component a), amides of α,β-ethylenically unsaturated mono- and dicarboxylic acids with $C_2$-$C_{30}$-amino alcohols which have a primary or secondary amino group, N-vinyllactams, N-vinylamides of saturated monocarboxylic acids, primary amides of α,β-ethylenically unsaturated monocarboxylic acids and N-alkyl and N,N-dialkyl derivatives thereof, which primary amides differ from component b), esters of vinyl alcohol and allyl alcohol with $C_1$-$C_{30}$-monocarboxylic acids, vinyl ethers, vinylaromatics, vinyl halides, vinylidene halides, $C_1$-$C_8$-monoolefins, nonaromatic hydrocarbons having at least two conjugated double bonds and mixtures thereof.

N-Vinyllactams suitable as monomers f) are unsubstituted N-vinyllactams and N-vinyllactam derivatives which may have, for example, one or more $C_1$-$C_6$-alkyl substituents, such as methyl, ethyl, n-propyl, isopropyl, n-butyl, sec-butyl, tert-butyl, etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam, etc. In a preferred embodiment, the novel copolymers comprise no N-vinyllactams incorporated in the form of polymerized units.

N-Vinylamide compounds suitable as monomers f) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide. In a preferred embodiment, the novel copolymers comprise no N-vinylamide compounds incorporated in the form of polymerized units.

Suitable additional monomers f) are furthermore 2-hydroxyethyl acrylate, 2-hydroxyethyl methacrylate, 2-hydroxyethylethacrylat, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate and 3-hydroxy-2-ethylhexyl methacrylate.

Suitable additional monomers f) are furthermore 2-hydroxyethylacrylamide, 2-hydroxyethylmethacrylamide, 2-hydroxyethylethacrylamide, 2-hydroxypropyl-acrylamide, 2-hydroxypropylmethacrylamide, 3-hydroxypropylacrylamide, 3-hydroxypropylmethacrylamide, 3-hydroxybutylacrylamide, 3-hydroxybutyl-methacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethylhexylmethacrylamide.

Suitable monomers f) are also polyetheracrylates, which, in the context of this invention, are understood as meaning generally esters of α,β-ethylenically unsaturated mono- and dicarboxylic acids with polyetherols. Suitable polyetherols are linear or branched substances which have terminal hydroxyl groups and comprise ether bonds. In general, they have a molecular weight of from about 150 to 20 000. Suitable polyetherols are polyalkylene glycols, such as polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin and 1,2- and 2,3-butylene oxide. The alkylene oxide copolymers may comprise the alkylene oxide units incorporated as random polymerized units or in the form of blocks. Ethylene oxide/propylene oxide copolymers are preferred.

Preferred components f) are polyetheracrylates of the formula II

where the alkylene oxide units have any desired sequence,
k and l, independently of one another, are each an integer from 0 to 1000, the sum of k and l being at least 5,
$R^4$ is hydrogen, $C_1$-$C_{30}$-alkyl or $C_5$-$C_8$-cycloalkyl,
$R^5$ is hydrogen or $C_1$-$C_8$-alkyl,
$Y^2$ is O or $NR^6$, $R^6$ being hydrogen, $C_1$-$C_{30}$-alkyl or $C_5$-$C_8$-cycloalkyl.
k is preferably an integer from 1 to 500, in particular from 3 to 250. l is preferably an integer from 0 to 100.
$R^5$ is preferably hydrogen, methyl, ethyl, n-propyl, isopropyl, n-butyl, sec-butyl, tert-butyl, n-pentyl or n-hexyl, in particular hydrogen, methyl or ethyl.
$R^4$ in the formula II is preferably hydrogen, methyl, ethyl, n-propyl, isopropyl, n-butyl, sec-butyl, n-pentyl, n-hexyl, octyl, 2-ethylhexyl, decyl, lauryl, palmityl or stearyl.
$Y^2$ in the formula II is preferably O or NH.

Suitable polyetheracrylates f) are, for example, the polycondensates of the abovementioned α,β-ethylenically unsaturated mono- and/or dicarboxylic acids and the acid chlorides, acid amides and anhydrides thereof with polyetherols. Suitable polyetherols can be readily prepared by reacting ethylene oxide, 1,2-propylene oxide and/or epichlorohydrin with an initiator molecule, such as water or a short-chain alcohol $R^4$—OH. The alkylene oxides may be used individually, alternately in succession or as a mixture. The polyetheracylates e) may be used alone or as mixtures for the preparation of the polymers used according to the invention.

Suitable additional monomers f) are methyl (meth)acrylate, methyl ethacrylate, ethyl (meth)acrylate, 2-pentyl (meth)acrylate, 3-pentyl (meth)acrylate, isopentyl acrylate, neopentyl acrylate, ethyl ethacrylate, isopropyl (meth)acrylate, n-butyl (meth)acrylate, sec-butyl (meth)acrylate, isobutyl (meth)acrylate, tert-butyl ethacrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth) acrylate, arrachinyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate and mixtures thereof. Preferred monomers e) are the esters of $\alpha,\beta$-ethylenically unsaturated mono- and dicarboxylic acids with $C_1$-$C_4$-alkanols.

Suitable additional monomers f) are furthermore N-(n-butyl)methacrylamide, N-(sec-butyl)methacrylamide, N-(tert-butyl)methacrylamide, N-(n-pentyl)(meth)acrylamide, N-(n-hexyl)(meth)acrylamide, N-(n-heptyl)(meth)acrylamide, N-(n-octyl)(meth)acrylamide, N-(tert-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)-(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth)acrylamide, N-heptadecyl(meth)acrylamide, N-nonadecyl(meth)acrylamide, N-arrachinyl-(meth)acrylamide, N-behenyl(meth)acrylamide, N-lignocerenyl(meth)acrylamide, N-cerotinyl(meth)acrylamide, N-melissinyl(meth)acrylamide, N-palmitoleinyl-(meth)acrylamide, N-oleyl(meth)acrylamide, N-linolyl (meth)acrylamide, N-linolenyl(meth)acrylamide, N-stearyl (meth)acrylamide, N-lauryl(meth)acrylamide.

Suitable additional monomers f) are furthermore vinyl acetate, vinyl propionate, vinyl butyrate and mixtures thereof.

Suitable additional monomers f) are furthermore ethylene, propylene, isobutylene, butadiene, styrene, $\alpha$-methylstyrene, acrylonitrile, methacrylonitrile, vinyl chloride, vinylidene chloride, vinyl fluoride, vinylidene fluoride and mixtures thereof.

The abovementioned additional monomers f) can be used individually or in the form of any desired mixtures.

The copolymers according to the invention preferably comprise, incorporated in the form of polymerized units, at least one compound f) which is selected from $C_1$-$C_3$-alkyl methacrylates, hydroxy-$C_1$-$C_3$-alkyl methacrylates and mixtures thereof. Ethyl methacrylate, hydroxyethyl methacrylate and mixtures thereof are particularly preferred. In particular, ethyl methacrylate is used. The copolymers according to the invention comprise these monomers, incorporated in the form of polymerized units, preferably in an amount of not more than 50% by weight, particularly preferably not more than 45% by weight, based on the total weight of compounds of component a) and these compounds f).

The novel copolymers preferably comprise up to 25, particularly preferably up to 20, in particular up to 15, % by weight, based on the total weight of the monomers used for the polymerization, of at least one monomer f) incorporated in the form of polymerized units. If a monomer f) is used, it is preferably used in an amount of at least 0.1, particularly preferably at least 1, in particular at least 5, % by weight.

Crosslinking Agent g)

The novel copolymers can, if desired, comprise at least one crosslinking agent, i.e. a compound having two or more than two ethylenically unsaturated nonconjugated double bonds, incorporated in the form of polymerized units.

Crosslinking agents are preferably used in an amount of from 0.01 to 3, particularly preferably from 0.1 to 2, % by weight, based on the total weight of the monomers used for the polymerization.

Suitable crosslinking agents g) are, for example, acrylates, methacrylates, allyl ethers or vinyl ethers of at least dihydric alcohols. Some or all of the OH groups of the parent alcohols may have been etherified or esterified; however, the crosslinking agents comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentylglycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, the monoester of neopentylglycol with hydroxypivalic acid, 2,2-bis (4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol and polyethylene glycols, polypropylene glycols and polytetrahydrofurans having molecular weights of in each case from 200 to 10 000. In addition to the homopolymers of ethylene oxide or of propylene oxide, block copolymers of ethylene oxide or propylene oxide or copolymers which comprise ethylene oxide and propylene oxide groups incorporated in the form of polymerized units may also be used. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose or mannose. Of course, the polyhydric alcohols may also be used after reaction with ethylene oxide or propylene oxide, in the form of the corresponding ethoxylates or propoxylates, respectively. The polyhydric alcohols may also first be converted into the corresponding glycidyl ethers by reaction with epichlorohydrin.

Further suitable crosslinking agents g) are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamic alcohol, citronellol, crotyl alcohol or cis-9-octadecen-1-ol. However, the monohydric, unsaturated alcohols may also be esterified with polyhydric carboxylic acids, for example malonic acid, tartaric acid, trimellitic acid, phthalic acid, terephthalic acid, citric acid or succinic acid.

Further suitable crosslinking agents g) are esters of unsaturated carboxylic acids with the polyhydric alcohols described above, for example oleic acid, crotonic acid, cinnamic acid or 10-undecenoic acid.

Further suitable crosslinking agents g) are urethane diacrylates and urethane polyacrylates, as commercially available, for example, under the name Laromer®.

Other suitable crosslinking agents g) are straight-chain or branched, linear or cyclic, aliphatic or aromatic hydrocarbons which have at least two double bonds which, in the case of aliphatic hydrocarbons, may be nonconjugated, e.g. divinylbenzene, divinyltoluene, 1,7-octadiene, 1,9-decadiene, 4-vinyl-1-cyclohexene, trivinylcyclohexane or polybutadienes having molecular weights of from 200 to 20 000.

Suitable crosslinking agents g) are furthermore the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Also suitable are the amides of allylamine and unsaturated carboxylic acids, such as acrylic acid, methacrylic acid, itaconic acid or maleic acid, or at least dibasic carboxylic acids, as described above.

Triallylamine and triallylmonoalkylammonium salts, e.g. triallylmethylammonium chloride or methylsulfate, are furthermore suitable as crosslinking agent g).

N-Vinyl compounds of urea derivatives, at least difunctional amides, cyanurates or urethanes, for example of urea, ethyleneurea, propyleneurea or tartaramide, e.g. N,N'-divinylethyleneurea or N,N'-divinylpropyleneurea, are also suitable.

Further suitable crosslinking agents g) are divinyldioxane, tetraallylsilane or tetravinylsilane.

Of course, mixtures of the abovementioned compounds g) may also be used. Water-soluble crosslinking agents g) are preferably used.

Particularly preferably used crosslinking agents g) are, for example, methylenebisacrylamide, triallylamine and triallylalkylammonium salts, divinylimidazole, pentaerythrityl triallyl ether, N,N'-divinylethyleneurea, reaction products of polyhydric alcohols with acrylic acid or methacrylic acid, methacrylates and acrylates of polyalkylene oxides or polyhydric alcohols which have been reacted with ethylene oxide and/or propylene oxide and/or epichlorohydrin.

Very particularly preferred crosslinking agents g) are pentaerythrityl triallyl ether, methylenebisacrylamide, N,N'-divinylethyleneurea, triallylamine and triallylmonoalkylammonium salts and acrylates of glycol, butanediol, trimethylolpropane and glycerol or acrylates of glycol, butanediol, trimethylolpropane or glycerol which has been reacted with ethylene oxide and/or epichlorohydrin.

Preferred copolymers are those which comprise
  from 30 to 90, particularly preferably from 40 to 85, % by weight of at least one compound a),
  from 3 to 50, particularly preferably from 5 to 40, in particular from 10 to 35, % by weight of at least one compound b),
  from 5 to 40, particularly preferably from 7 to 35, in particular from 10 to 30, % by weight of acrylic acid c),
  from 0 to 25, particularly preferably from 1 to 20, in particular from 5 to 15, % by weight of methacrylic acid d),
  from 0 to 25, particularly preferably from 1 to 20, in particular from 2 to 10, % by weight of at least one compound e),
  from 0 to 25, particularly preferably from 0.1 to 20, in particular from 5 to 15, % by weight of at least one compound f),
  from 0 to 5, particularly preferably from 0.01 to 3, in particular from 0.1 to 2, % by weight of at least one crosslinking agent g), incorporated in the form of polymerized units.

A preferred embodiment comprises copolymers which consist of repeating units of
  tert-butyl acrylate,
  methacrylamide and/or N-(tert-butyl)acrylamide and
  acrylic acid.

A further preferred embodiment comprises copolymers which consist of repeating units of
  tert-butyl acrylate,
  methacrylamide and/or N-(tert-butyl)acrylamide,
  acrylic acid and
  methacrylic acid.

A further preferred embodiment comprises copolymers which consist of repeating units of
  tert-butyl acrylate,
  N-acryloylmorpholine or N,N-dimethylacrylamide and
  acrylic acid.

A further preferred embodiment comprises copolymers which consist of repeating units of
  tert-butyl acrylate,
  methacrylamide and/or N-(tert-butyl)acrylamide and/or N-acryloylmorpholine and/or N,N-dimethylacrylamide and
  acrylic acid.

A further preferred embodiment comprises copolymers which consist of repeating units of
  tert-butyl acrylate,
  methacrylamide and/or N-(tert-butyl)acrylamide and/or N-acryloylmorpholine and/or N,N-dimethylacrylamide,
  acrylic acid and
  methacrylic acid.

A further preferred embodiment comprises copolymers which consist of repeating units of
  tert-butyl acrylate,
  methacrylamide and/or N-(tert-butyl)acrylamide,
  N-vinylpyrrolidone and
  acrylic acid.

A further preferred embodiment comprises copolymers which consist of repeating units of
  tert-butyl acrylate,
  methacrylamide and/or N-(tert-butyl)acrylamide,
  N-vinylpyrrolidone,
  acrylic acid and
  methacrylic acid.

A further preferred embodiment comprises copolymers which consist of repeating units of
  tert-butyl acrylate,
  tert-butyl methacrylate,
  methacrylamide and/or N-(tert-butyl)acrylamide and
  acrylic acid.

A further preferred embodiment comprises copolymers which consist of repeating units of
  tert-butyl acrylate,
  tert-butyl methacrylate,
  methacrylamide and/or N-(tert-butyl)acrylamide,
  acrylic acid and
  methacrylic acid.

A further preferred embodiment comprises copolymers which consist of repeating units of
  tert-butyl acrylate and/or tert-butyl methacrylate,
  methacrylamide and/or N-(tert-butyl)acrylamide,
  acrylic acid and
  N-(tert-butyl)aminoethyl (meth)acrylate or N-[3-(dimethylamino)propyl]-methacrylamide or N-vinylimidazole.

A further preferred embodiment comprises copolymers which consist of repeating units of
tert-butyl acrylate and/or tert-butyl methacrylate,
methacrylamide and/or N-(tert-butyl)acrylamide,
acrylic acid,
methacrylic acid and
N-(tert-butyl)aminoethyl (meth)acrylate or N-[3-(dimethylamino)propyl]-methacrylamide or N-vinylimidazole.

Copolymers which comprise, incorporated in the form of polymerized units,
a) tert-butyl acrylate and/or tert-butyl methacrylate,
b) methacrylamide and/or N-(tert-butyl)acrylamide,
c) acrylic acid and
f) at least one compound which is selected from $C_1$-$C_3$-alkyl methacrylates, hydroxy-$C_1$-$C_3$-alkyl methacrylates and mixtures thereof are furthermore preferred, with the proviso that the proportion by weight of component a) is equal to or greater than the proportion by weight of component f).

A preferred embodiment comprises copolymers which comprise, incorporated in the form of polymerized units,
a) tert-butyl acrylate,
b) methacrylamide and/or N-(tert-butyl)acrylamide,
c) acrylic acid,
d) methacrylic acid,
f) ethyl methacrylate and/or hydroxyethyl methacrylate, with the proviso that the proportion by weight of component a) is equal to or greater than the proportion by weight of component f).

A particularly preferred embodiment comprises copolymers which consist of repeating units of
tert-butyl acrylate,
methacrylamide and/or N-(tert-butyl)acrylamide,
acrylic acid and
ethyl methacrylate, with the proviso that the proportion by weight of tert-butyl acrylate is equal to or greater than the proportion by weight of ethyl methacrylate.

A further particularly preferred embodiment comprises copolymers which consist of repeating units of
tert-butyl acrylate,
methacrylamide and/or N-(tert-butyl)acrylamide,
acrylic acid,
methacrylic acid and
ethyl methacrylate, with the proviso that the proportion by weight of tert-butyl acrylate is equal to or greater than the proportion by weight of ethyl methacrylate.

Copolymers which comprise, based in each case on the total weight of the monomers used for the polymerization,
from 40 to 80% by weight, preferably from 45 to 75% by weight, of tert-butyl acrylate and ethyl methacrylate, with the proviso that the proportion by weight of tert-butyl methacrylate is equal to or greater than the proportion by weight of ethyl methacrylate,
from 5 to 30% by weight, preferably from 7 to 25% by weight, of methacrylamide and/or N-(tert-butyl)acrylamide,
from 5 to 30% by weight, preferably from 5 to 15% by weight, of acrylic acid and
from 0 to 25% by weight, preferably from 5 to 20% by weight, of methacrylic acid incorporated in the form of polymerized units are preferred.

The preparation of the novel copolymers can be effected, for example, by solution, precipitation, suspension or emulsion polymerization. Such processes are known in principle to a person skilled in the art. The preparation by solution polymerization is preferred.

Preferred solvents for the polymerization are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of the dihydric alcohols, diethylene glycol, triethylene glycol, polyethylene glycols having number average molecular weights of up to about 3000, glycerol and dioxane. Polymerization in water or a water/alcohol mixture, for example in a water/ethanol mixture, is particularly preferred.

The polymerization can be effected in principle at the pH produced by the monomers used. If at least one N-vinyllactam is used for the polymerization (=component f)), the pH of the polymerization medium is preferably brought to 5 to 8, preferably 6 to 7. It is advantageous subsequently to keep the pH in this range during the polymerization. All inorganic or organic bases (and, if appropriate, acids), in particular those which, apart from any salt formation, undergo no reaction with the monomers, are suitable in principle for establishing the pH before, during or after the polymerization. Suitable bases are, for example, alkali metal and alkaline earth metal hydroxides, ammonia and primary, secondary and tertiary amines, such as triethylamine, and amino alcohols, such as triethanolamine, methyldiethanolamine, dimethylethanolamine or 2-amino-2-methylpropanol. At least one tertiary amine which is selected in particular from N,N-dimethylethanolamine, N-methyldiethanolamine, triethanolamine and mixtures thereof is preferably used for establishing the pH. If at least one N-vinyllactam is used for the polymerization (=component f)), a pH of the polymerization medium is preferably established with N,N-dimethylethanolamine.

The polymerization temperatures are preferably from about 30 to 120° C., particularly preferably from 40 to 100° C. The polymerization is usually effected under atmospheric pressure but may also take place under reduced or superatmospheric pressure. A suitable pressure range is from 1 to 5 bar.

For the copolymerization, the monomers can be polymerized with the aid of free radical initiators.

Initiators which may be used for the free radical polymerization are the peroxo and/or azo compounds customary for this purpose, for example alkali metal or ammonium peroxodisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumyl hydroperoxide, diisopropyl peroxodicarbamate, bis(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis(2-amidinopropane) hydrochloride (V50 from Wako Pure Chemicals Industries, Ltd.) or 2,2'-azobis(2-methyl-butyronitrile). Initiator mixtures or redox initiator systems, e.g. ascorbic acid/iron(II) sulfate/sodium peroxodisulfate, tert-butyl hydroperoxide/sodium disulfite, tert-butyl hydroperoxide/sodium hydroxymethanesulfinate or $H_2O_2/Cu^I$, are also suitable.

For establishing the molecular weight, the polymerization can be effected in the presence of at least one regulator. Regulators which may be used are the conventional compounds known to a person skilled in the art, such as sulfur compounds, e.g. mercaptoethanol, 2-ethylhexyl thioglycolate, thioglycolic acid or dodecyl mercaptan, and tribromochloromethane or other compounds which have a regulating effect on the molecular weight of the polymers obtained. A preferred regulator is cysteine.

In order to obtain very pure polymers having a low residual monomer content, the polymerization (main polymerization) may be followed by a postpolymerization step. The postpolymerization can be effected in the presence of the same initiator system as the main polymerization or of an initiator system differing therefrom. Preferably, the postpolymerization is effected at least at the same temperature as the main polymerization, preferably at a higher temperature than the main polymerization. If desired, the reaction batch can be subjected to stripping with steam or to a steam distillation after the polymerization or between the first and the second polymerization step.

If an organic solvent is used in the preparation of the polymers, this can be removed by conventional methods known to a person skilled in the art, e.g. by distillation at reduced pressure.

The liquid polymer compositions obtained can be converted into powder form by various drying methods, e.g. spray drying, fluidized spray drying, drum drying or freeze drying. Spray drying is preferably used. The dry polymer powders thus obtained can advantageously be converted into an aqueous solution or dispersion again by dissolution or redispersing in water. Copolymer powders have the advantage of better storability and easier transportability and as a rule have less tendency to attack by germs. These include very generally anionic, cationic, amphoteric and neutral polymers.

The copolymers described above are very useful for the preparation of cosmetic and pharmaceutical compositions. They serve, for example, as polymeric film formers in formulations for personal hygiene, which includes use in cosmetic formulations for keratinous surfaces, such as skin, hair and nails, and also oral hygiene preparations. They can be used and formulated universally in a very wide range of cosmetic formulations and are compatible with the conventional components. The novel copolymers are particularly suitable for the preparation of cosmetic hair compositions. Compared with conventional polymers known from the prior art, they are advantageously suitable for the production of elastic hairstyles in combination with strong setting (also at high atmospheric humidity). The novel copolymers also have good propellant compatibility, good solubility in water or aqueous/alcoholic solvent mixtures and suitability for use in low-VOC formulations and can be readily washed out. Moreover, they have as a rule good conditioning properties, i.e. they improve hair treated therewith in its sensory properties, such as handle, body, handleability, etc. Hair spray formulations based on the novel copolymers have good rheological properties and good sprayability.

Cosmetically acceptable carriers B)

The novel compositions comprise a cosmetically or pharmaceutically acceptable carrier B) which is selected from
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with monohydric, dihydric or trihydric alcohols, which esters differ from iii),
v) saturated acyclic and cyclic hydrocarbons,
vi) fatty acids,
vii) fatty alcohols,
viii) propellants and mixtures thereof.

The novel compositions comprise, for example, an oil or fat component B) which is selected from: hydrocarbons of low polarity, such as mineral oils; linear saturated hydrocarbons, preferably of more than 8 carbon atoms, such as tetradecane, hexadecane, octadecane, etc.; cyclic hydrocarbons, such as decahydronaphthalene; branched hydrocarbons; animal and vegetable oils; waxes; wax esters; Vaseline; esters, preferably esters of fatty acids, e.g. the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylates; benzoate esters, such as $C_{10}$-$C_{15}$-alkylbenzoates, benzyl benzoate; other cosmetic esters, such as fatty acid triglycerides, propylene glycol monolaurate, polyethylene glycol monolaurate, $C_{10}$-$C_{15}$-alkyllactates, etc., and mixtures thereof.

Suitable silicone oils B) are, for example, linear polydimethylsiloxanes, poly(methylphenylsiloxanes), cyclic siloxanes and mixtures thereof. The number average molecular weight of the polydimethylsiloxanes and poly(methylphenylsiloxanes) is preferably from about 1000 to 150 000 g/mol. Preferred cyclic siloxanes have 4- to 8-membered rings. Suitable cyclic siloxanes are commercially available, for example, under the name cyclomethicone.

Preferred oil or fat components B) are selected from paraffin and liquid paraffins; Vaseline; natural fats and oils, such as castor oil, soybean oil, peanut oil, olive oil, sunflower oil, sesame oil, avocado oil, cocoa butter, almond oil, peach kernel oil, Ricinus communis oil, cod liver oil, lard, spermaceti, sperm oil, wheat germ oil, macadamia nut oil, evening primrose oil, jojoba oil; fatty alcohols, such as lauryl alcohol, myristyl alcohol, cetyl alcohol, stearyl alcohol, oleyl alcohol; fatty acids, such as myristic acid, stearic acid, palmitic acid, oleic acid, linoleic acid, linolenic acid and saturated, unsaturated and substituted fatty acids differing therefrom; waxes, such as beeswax, carnauba wax, candelilla wax, spermaceti and mixtures of the abovementioned oil or fat components.

Suitable cosmetically and pharmaceutically compatible oil or fat components B) are described in Karl-Heinz Schrader, Grundlagen und Rezepturen der Kosmetika, 2nd Edition, Verlag Huthig, Heidelberg, pages 319-355, which is hereby incorporated by reference.

Suitable hydrophilic carriers B) are selected from water, monohydric, dihydric or polyhydric alcohols of, preferably, 1 to 8 carbon atoms, such as ethanol, n-propanol, isopropanol, propylene glycol, glycerol, sorbitol, etc.

The novel cosmetic compositions may be cosmetic skin compositions, cosmetic hair compositions or dermatological, hygiene or pharmaceutical compositions. Owing to their film-forming properties, the copolymers and polyelectrolyte complexes described above are suitable in particular as additives for hair and skin cosmetics.

The novel compositions are preferably in the form of a spray, gel, foam, ointment, cream, emulsion, suspension, lotion, milk or paste. If desired, liposomes or microspheres may also be used.

The novel cosmetically or pharmaceutically active compositions may additionally comprise cosmetically and/or dermatologically active substances and excipients.

The novel cosmetic compositions preferably comprise at least one copolymer (=component A) as defined above, at least one carrier B) as defined above and at least one component which differs therefrom and is selected from cosmetically active substances, emulsifiers, surfactants, preservatives, perfume oils, thickeners, hair polymers, hair and skin conditioners, graft polymers, water-soluble or dispersible silicone-containing polymers, light stabilizers, bleaches, gel formers, care compositions, colorants, tinting compositions, tanning compositions, dyes, pigments, consistency agents, humidifiers, refatting agents, collagen, protein hydrolysis products, lipids, antioxidants, antifoams, antistatic agents, emollients and softeners.

Conventional thickeners in such formulations are crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. Nonionic thickeners are preferably used.

Suitable cosmetically and/or dermatologically active substances are, for example, color-imparting active substances, skin and hair pigmenting compositions, tinting compositions, tanning compositions, bleaches, keratin-hardening substances, antimicrobial active substances, light filter active substances, repellent active substances, substances having a hyperemic effect, keratolytic and keratoplastic substances, antidandruff active substances, antiphlogistic agents, substances having a keratinizing effect, antioxidants or substances active as free radical scavengers, substances which moisturize the skin or keep it moist, refatting active substances, antierythematous or antiallergic active substances and mixtures thereof.

Artificially skin-tanning active substances which are suitable for tanning the skin without natural or artificial exposure to UV rays are, for example, dihydroxyacetone, alloxane and walnut shell extract. Suitable keratin-hardening substances are as a rule active substances as also used in antiperspirants, e.g. potassium aluminum sulfate, aluminum hydroxychloride, aluminum lactate, etc. Antimicrobial active substances are used for destroying microorganisms or inhibiting their growth and thus serve both as preservatives and as deodorants which reduce the formation or the intensity of body odor. These include, for example, conventional preservatives known to a person skilled in the art, such as p-hydroxybenzoates, imidazolidinylurea, formaldehyde, sorbic acid, benzoic acid, salicylic acid, etc. Such deodorants are, for example, zinc ricinoleate, triclosan, undecylenoic acid alkylolamides, triethyl citrate, chlorhexidine, etc. Suitable light filter active substances are substances which absorb UV rays in the UV-B and/or UV-A range. Suitable UV filters are, for example, 2,4,6-triaryl-1,3,5-triazines in which the aryl groups may each carry at least one substituent which is preferably selected from hydroxyl, alkoxy, especially methoxy, alkoxycarbonyl, especially methoxycarbonyl and ethoxycarbonyl, and mixtures thereof. p-Aminobenzoates, cinnamic esters, benzophenones, camphor derivatives and pigments which provide screening from UV rays, such as titanium dioxide, talc and zinc oxide, are furthermore suitable. Suitable repellent active substances are compounds which are capable of keeping certain animals, in particular insects, away from humans, or of repelling them. These include, for example, 2-ethyl-1,3-hexanediol, N,N-diethyl-n-toluamide, etc. Suitable substances which have a hyperemic effect and stimulate blood flow in the skin are, for example, essential oils, such as dwarf pine-needle oil, lavender, rosemary, juniper, horse chestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active substances are, for example, sulfur, sulfur-polyethylene glycol sorbitan monooleate, sulfur-ricinol polyethoxylate, pyrithione zinc, pyrithione aluminum, etc. Suitable antiphlogistic agents which counteract skin irritations are, for example, allantoin, bisabolol, dragosantol, chamomile extract, panthenol, etc.

The novel cosmetic compositions may comprise at least one cosmetically or pharmaceutically acceptable polymer as a cosmetic and/or pharmaceutical active substance (as well as, if appropriate, as an excipient).

Anionic polymers preferred as additional polymers are, for example, homo- and copolymers of acrylic acid and methacrylic acid and salts thereof. These also include crosslinked polymers of acrylic acid, as available under the INCI name carbomer. Such crosslinked homopolymers of acrylic acid are commercially available, for example, under the name Carbopol® from BF GOODRICH. Hydrophobically modified crosslinked polyacrylate polymers, such as Carbopol® Ultrez 21 from Noveon, are also preferred.

Further examples of suitable additional anionic polymers are copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of (meth)acrylic acid and polyetheracrylates, the polyether chain being terminated by a $C_8$-$C_{30}$-alkyl radical. These include, for example, acrylate/beheneth-25 methacrylate copolymers, which are available under the name Aculyn® from Rohm und Haas. Particularly suitable polymers are furthermore copolymers of tert-butyl acrylate, ethyl acrylate, methacrylic acid (e.g. Luvimer® 100P), copolymers of ethyl acrylate and methacrylic acid (e.g. Luviumer® MAE), copolymers of N-tert-butylacrylamide, ethyl acrylate, acrylic acid (Ultrahold® 8, strong), copolymers of vinyl acetate, crotonic acid and, if appropriate, further vinyl esters (e.g. Luviset® brands), maleic anhydride copolymers, if appropriate reacted with alcohol, anionic polysiloxanes, e.g. carboxy-functional, tert-butyl acrylate, methacrylic acid (e.g. Luviskol® VBM), copolymers of acrylic acid and methacrylic acid with hydrophobic monomers, such as $C_4$-$C_{30}$-alkyl esters of (meth)acrylic acid, $C_4$-$C_{30}$-alkyl vinyl esters, $C_4$-$C_{30}$-alkyl vinyl ethers and hyaluronic acid. Examples of anionic polymers are furthermore vinyl acetate/crotonic acid copolymers, as commercially available, for example, under the name Resyn® (National Starch) and Gafset® (GAF), and vinylpyrrolidone/vinyl acrylate copolymers, available, for example, under the trade name Luviflex® (BASF). Further suitable polymers are the vinylpyrrolidone/acrylate terpolymer available under the, name Luviflex® VBM-35 (BASF) and sodium sulfonate-containing polyamides or sodium sulfonate-containing polyesters.

The group consisting of the suitable anionic polymers furthermore comprises, for example, Balance® CR (National Starch; acrylate copolymer), Balance® 0/55 (National Starch; acrylate copolymer), Balance® 47 (National Starch; octylacrylamide/acrylate/butylaminoethyl methacrylate copolymer), Aquaflex® FX 64 (ISP; isobutylene/ethylmaleimide/hydroxyethylmaleimide copolymer), Aquaflex® SF-40 (ISP/National Starch; VP/vinyl caprolactam/DMAPA acrylate copolymer), Allianz® LT-120 (ISP; Rohm & Haas; acrylate/C1-2 succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-712 (Clariant; methacryloylethyl N-oxide/methacrylate copolymer), Omnirez® 2000 (ISP; monoethyl ester of poly(methyl vinyl ether/maleic acid in ethanol), Amphomer® HC (National Starch; acrylate/octylacrylamide copolymer), Amphomer® 28-4910 (National Starch; octylacrylamide/acrylate/butylaminoethyl methacrylate copolymer), Advantage® HC 37 (ISP; terpolymer of vinylcaprolactam/vinylpyrrolidone/dimethylaminoethyl methacrylate), Advantage® LC55 and LC80 or LC A and LC E, Advantage® Plus (ISP; VA/butyl maleate/isobornyl acrylate copolymer), Aculyne® 258 (Rohm & Haas; acrylate/hydroxyester acrylate copolymer), Luviset® P.U.R. (BASF, polyurethane-1), Luviflex® Silk (BASF), Eastman® AQ 48 (Eastman), Styleze® CC-10 (ISP; VP/DMAPA acrylates copolymer), Styleze® 2000 (ISP; VP/acrylates/lauryl methacrylate copolymer), DynamX (National Starch; polyurethane-14 AMP-acrylates copolymer), Resyn XP (National Starch; acrylates/octylacrylamide copolymer), Fixomer A-30 (Ondeo Nalco; polymethacrylic acid (and) acrylamidomethylpropanesulfonic acid), Fixate G-100 (Noveon; AMP-acrylates/allyl methacrylate copolymer).

Suitable additional polymers are also the terpolymers described in U.S. Pat. No. 3,405,084 and obtained from vinylpyrrolidone, $C_1$-$C_{10}$-alkyl, cycloalkyl and aryl (meth) acrylates and acrylic acid. Suitable additional polymers are furthermore the terpolymers described in EP-A-0 257 444 and EP-A-0 480 280 and obtained from vinylpyrrolidone, tert-butyl (meth)acrylate and (meth)acrylic acid. Suitable additional polymers are furthermore the copolymers described in DE-A-42 23 066 and comprising at least one (meth)acrylate, (meth)acrylic acid and N-vinylpyrrolidone and/or N-vinylcaprolactam incorporated in the form of polymerized units. Reference is hereby made to the disclosure of these documents.

Suitable carboxyl-containing polymers are furthermore carboxyl-containing polyurethanes.

EP-A-636361 discloses suitable block copolymers having polysiloxane blocks and polyurethane/polyurea blocks, which have carboxyl and/or sulfo groups. Suitable silicone-containing polyurethanes are also described in WO 97/25021 and EP-A-751 162. Suitable polyurethanes are also described in DE-A-42 25 045, which is hereby incorporated by reference in its entirety. These polyurethanes are in principle composed of i) at least one compound which comprises two or more active hydrogen atoms per molecule,
ii) at least one carboxyl-comprising diol or a salt thereof and
iii) at least one polyisocyanate.

The component i) comprises, for example, diols, diamines, amino alcohols and mixtures thereof. The molecular weight of these compounds is preferably from about 56 to 280. If desired, up to 3 mol % of said compounds may be replaced by triols or triamines.

Useable diols i) are, for example, ethylene glycol, propylene glycol, butylene glycol, neopentylglycol, cyclohexanedimethylol, di-, tri-, tetra-, penta- or hexaethylene glycol and mixtures thereof. Neopentylglycol and/or cyclohexanedimethylol are preferably used. Suitable amino alcohols i) are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol, etc. Suitable diamines i) are, for example, ethylenediamine, propylenediamine, 1,4-diaminobutane, 1,5-diaminopentane and 1,6-diaminohexane, and α,ω-diaminopolyethers which can be prepared by aminating polyalkylene oxides with ammonia.

The components i) may also be a polymer having a number average molecular weight of from about 300 to 5000, preferably from about 400 to 4000, in particular from 500 to 3000. Useable polymers i) are, for example, polyesterdiols, polyetherols and mixtures thereof. Polyetherols are preferably polyalkylene glycols, e.g. polyethylene glycols, polypropylene glycols, polytetrahydrofurans, etc., block copolymers of ethylene oxide and propylene oxide or block copolymers of ethylene oxide, propylene oxide and butylene oxide, which comprise the alkylene oxide units incorporated in the form of random polymerized units or in the form of blocks. Suitable polytetrahydrofurans i) can be prepared by cationic polymerization of tetrahydrofuran in the presence of acidic catalysts, e.g. sulfuric acid or fluorosulfuric acid. Such preparation processes are known to a person skilled in the art. Useable polyesterdiols i) preferably have a number average molecular weight of from about 400 to 5000, preferably from 500 to 3000, in particular from 600 to 2000. Suitable polyesterdiols i) are all those which are usually used for the preparation of polyurethanes, in particular those based on aromatic dicarboxylic acids, such as terephthalic acid, isophthalic acid, phthalic acid, sodium or potassium sulfoisophthalate, etc., aliphatic dicarboxylic acids, such as adipic acid or succinic acid, etc., and cycloaliphatic dicarboxylic acids, such as 1,2-, 1,3- or 1,4-cyclohexanedicarboxylic acid. Particularly suitable diols are aliphatic diols, such as ethylene glycol, propylene glycol, 1,6-hexanediol, neopentylglycol, diethylene glycol, polyethylene glycols, polypropylene glycols, 1,4-dimethylolcyclohexane, etc.

Suitable compounds ii) which have two active hydrogen atoms and at least one carboxyl group per molecule are, for example, dimethylolpropanoic acid and mixtures which comprise dimethylolpropanoic acid.

The components iii) comprise conventional aliphatic, cycloaliphatic and/or aromatic polyisocyanates, such as tetramethylene diisocyanate, hexamethylene diisocyanate, methylenediphenyl diisocyanate, toluene 2,4- and 2,6-diisocyanate and isomer mixtures thereof, o- and m-xylylene diisocyanate, naphthylene 1,5-diisocyanate, cyclohexylene 1,4-diisocyanate, dicyclohexylmethane diisocyanate and mixtures thereof, in particular isophorone diisocyanate and/or dicyclohexylmethane diisocyanate. If desired, up to 3 mol % of said compounds may be replaced by triisocyanates.

Suitable additional polymers are furthermore cationic polymers. These include, for example, polymers having the name polyquaternium according to INCI, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaterhium-4 and -10), acrylamido copolymers (polyquaternium-7) and chitosan. Suitable cationic (quaternized) polymers are also Merquat® (polymer based on dimethyldiallylammonium chloride), Gafquat® (quaternized polymers which are formed by reaction of polyvinylpyrrolidone with quaternary ammonium compounds), polymer JR (hydroxyethylcellulose having cationic groups) and plant-based cationic polymers, e.g. guar polymers, such as the Jaguar® brands from Rhodia.

Suitable additional polymers are also amphoteric or zwitterionic polymers, such as the octylacrylamide/methyl methacrylate/tert-butylaminoethyl methacrylate/2-hydroxypropyl methcrylate copolymers available under the name Amphomer® (National Starch) and zwitterionic polymers as disclosed, for example, in German Patent Applications DE 39 29 973, DE 21 50 557, DE 28 17 369 and DE 37 08 451. Acrylamidopropyltrimethylammonium chloride/acrylic acid or methacrylic acid copolymers and the alkali metal and ammonium salts thereof are preferred zwitterionic polymers. Further suitable zwitterionic polymers are methacryloylethylbetaine/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®).

Neutral polymers suitable as additional polymers are, for example, polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethylenimines and salts thereof, polyvinylamines and salts thereof, cellulose derivatives, polyaspartic acid salts and derivatives. These include, for example, Luviflex® Swing (partly hydrolyzed copolymer of polyvinyl acetate and polyethylene glycol, from BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, for example based on itaconic acid and aliphatic diamines, as described, for example, in DE-A43 33 238.

Other suitable polymers are nonionic, siloxane-containing, water-soluble or water-dispersible polymers, e.g. polyethersiloxanes, such as Tegopren® (from Goldschmidt) or Belsil® (from Wacker).

The formulation base of novel pharmaceutical compositions preferably comprises pharmaceutically acceptable excipients. Pharmaceutically acceptable are the excipients which are known to be useable in pharmacy, food technology and ancillary areas, in particular the excipients listed in relevant pharmacopoeias (e.g. DAB, Ph. Eur., BP, NF), and other excipients whose properties do not prevent physiological use.

Suitable excipients may be: lubricants, wetting agents, emulsifying and suspending media, preservatives, antioxidants, anti-irritant substances, chelating agents, emulsion stabilizers, film formers, gel formers, odor masking compositions, resins, hydrocolloids, solvents, solubilizers, neutralizing agents, permeation accelerators, pigments, quaternary ammonium compounds, refatting and overfatting agents, ointment, cream or oil bases, silicone derivatives, stabilizers, sterilizers, propellants, drying agents, opacifiers, thickeners, waxes, softeners, white oils. A relevant embodiment is based on the knowledge of a person skilled in the art, as described, for example, in Fiedler, H. P. Lexikon der Hilfsstoffe fur Pharmazie, Kosmetik und angrenzende Gebiete, 4th Edition, Aulendorf: ECV-Editio-Kantor-Verlag, 1996.

For the preparation of the novel dermatological compositions, the active substances may be mixed or diluted with a suitable excipient. Excipients may be solid, semisolid or liquid materials which may serve as a vehicle, carrier or medium for the active substance. The admixing of further excipients is effected, if desired, in a manner known to a person skilled in the art. Furthermore, the polymers and polyelectrolyte complexes are suitable as excipients in pharmacy, preferably as or in coating material(s) or binder(s) for solid dosage forms. They can also be used in creams and as tablet coating materials and tablet binders.

According to a preferred embodiment, the novel compositions are a skin cleansing composition.

Preferred skin cleansing compositions are soaps of liquid to gel-like consistency, such as transparent soaps, luxury soaps, deodorant soaps, cream soaps, baby soaps, skin protection soaps, abrasive soaps and syndets, pasty soaps, spreading soaps and wash pastes, liquid wash, shower and bath preparations, such as wash lotions, shower baths and gels, foam baths, oil baths and scrubbing preparations, and shaving foams, lotions and creams.

According to a further preferred embodiment, the novel compositions are cosmetic compositions for the care and protection of skin, nail care compositions or formulations for decorative cosmetics.

Suitable cosmetic skin compositions are, for example, face lotions, face masks, deodorants and other cosmetic lotions. Compositions for use in decorative cosmetics comprise, for example, masking sticks, stage make-up, mascara and eye shadow, lipsticks, kajal pencils, eyeliners, rouges, powders and eyebrow pencils.

In addition, the novel copolymers can be used in nose strips for pore cleansing, in anti-acne compositions, repellents, shaving compositions, depilatory compositions, feminine hygiene compositions and foot care compositions and in baby care.

The novel skin care compositions are in particular W/O or O/W skin creams, day and night creams, eye creams, face creams, anti-wrinkle creams, moisturizing creams, bleaching creams, vitamin creams, skin lotions, care lotions and moisturizing lotions.

Cosmetic skin and dermatological compositions based on the copolymers described above have advantageous effects. The polymers can contribute, inter alia, to moistening and conditioning of the skin and to improvement of the skin sensation. The polymers can also act as thickeners in the formulations. By adding the novel polymers, a considerable improvement in the skin tolerance can be achieved in certain formulations.

Cosmetic skin and dermatological compositions preferably comprise at least one copolymer in an amount of from about 0.001 to 30, preferably from 0.01 to 20, very particularly preferably from 0.1 to 12, % by weight, based on the total weight of the composition.

In particular, light stabilizers based on the novel copolymers have the property of increasing the residence time of the UV-absorbing ingredients in comparison with conventional excipients, such as polyvinylpyrrolidone.

Depending on the field of use, the novel compositions can be applied in a form suitable for skin care, for example as cream, foam, gel, stick, mousse, milk, spray (pump spray or propellant-containing spray) or lotion.

In addition to the novel copolymers and suitable carriers, the cosmetic skin formulations may also comprise further active substances and excipients customary in skin cosmetics, as described above. These preferably include emulsifiers, preservatives, perfume oils, cosmetic active substances, such as phytantriol, vitamin A, E and C, retinol, bisabolol, panthenol, light stabilizers, bleaches, colorants, tinting compositions, tanning compositions, collagen, protein hydrolysis products, stabilizers, pH regulators, dyes, salts, thickeners, gel formers, consistency agents, silicones, moisturizers, refatting agents and further conventional additives.

Preferred oil and fat components of the cosmetic skin and dermatological compositions are the abovementioned mineral and synthetic oils, e.g. paraffins, silicone oils and aliphatic hydrocarbons of more than 8 carbon atoms, animal and vegetable oils, e.g. sunflower oil, coconut oil, avocado oil, olive oil or lanolin, or waxes, fatty acids, fatty esters, such as triglycerides of $C_6$-$C_{30}$-fatty acids, wax esters, such as jojoba oil, fatty alcohols, Vaseline, hydrogenated lanolin and acetylated lanolin and mixtures thereof.

The novel copolymers can also be mixed with conventional polymers if it is intended to establish special properties.

For establishing specific properties, for example improving the feel, the spreading behavior, the water resistance and/or the binding of active substances and excipients, such as pigments, the cosmetic skin and dermatological formulations may additionally comprise conditioning substances based on silicone compounds. Suitable silicone compounds are, for example, polyalkylsiloxanes, polyarylsiloxanes, polyarylalkylsiloxanes, polyethersiloxanes or silicone resins.

The preparation of the cosmetic or dermatological formulations is effected by conventional processes known to a person skilled in the art.

The cosmetic and dermatological compositions are preferably in the form of emulsions, in particular in the form of water-in-oil (W/O) or oil-in-water (O/W) emulsions. However, it is also possible to choose other formulation types, for example hydrodispersions, gels, oils, oleogels, multiple emulsions, for example in the form of W/O/W or O/W/O emulsions, anhydrous ointments or ointment bases, etc.

The preparation of emulsions is effected by known methods. In addition to at least one novel copolymer, the emulsions comprise, as a rule, conventional components, such as fatty alcohols, fatty esters and in particular fatty acid triglycerides, fatty acids, lanolin and derivatives thereof, natural or synthetic oils or waxes and emulsifiers in the presence of water. The choice of the additives specific to the emulsion type and the preparation of suitable emulsions is described, for example, in Schrader, Grundlagen und Rezepturen der Kosmetika, Hothig Buch Verlag, Heidelberg, 2nd Edition, 1989, third part, which is hereby incorporated by reference.

A suitable emulsion, for example for a skin cream, etc., generally comprises an aqueous phase, which is emulsified by means of a suitable emulsifier system in an oil or fat phase. For providing the aqueous phase, a novel copolymer may be used.

Preferred fat components which may be present in the fat phase of the emulsions are: hydrocarbon oils, such as liquid paraffin, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils which begin to distill under atmospheric pressure at about 250° C. and the end point of whose distillation is 410° C., e.g. Vaseline oil; esters of saturated or unsaturated fatty acids, such as alkyl myristates, e.g. isopropyl, isobutyl or cetyl myristate, hexadecyl stearate, ethyl or isopropyl palmitate, octanoic or decanoic acid triglycerides and cetyl ricinoleate.

The fat phase may also comprise silicone oils soluble in other oils, such as dimethylpolysiloxane, methylphenylpolysiloxane and the silicone-glycol copolymer, fatty acids and fatty alcohols.

In addition to the novel copolymers, it is also possible to use waxes, e.g. carnauba wax, candelilla wax, beeswax, microcrystalline wax, ozokerite wax and calcium, magnesium and aluminum oleates, myristates, linoleates and stearates.

Furthermore, a novel emulsion may be present in the form of an O/W emulsion. An emulsion of this type usually comprises an oil phase, emulsifiers which stabilize the oil phase in the aqueous phase, and an aqueous phase which is usually present in thickened form. Preferred emulsifiers are O/W emulsifiers, such as polyglyceryl esters, sorbitan esters or partly esterified glycerides.

According to a further preferred embodiment, the novel compositions are a shower gel, a shampoo formulation or a bath preparation.

Such formulations comprise at least one novel copolymer and usually anionic surfactants as base surfactants and amphoteric and/or nonionic surfactants as cosurfactants. Further suitable active substances and/or excipients are generally selected from lipids, perfume oils, dyes, organic acids, preservatives and antioxidants and thickeners/gel formers, skin conditioners and moisturizers.

These formulations preferably comprise from 2 to 50, preferably from 5 to 40, particularly preferably from 8 to 30, % by weight, based on the total weight of the formulation, of surfactants.

In the wash, shower and bath preparations, it is possible to use all anionic, neutral, amphoteric or cationic surfactants usually employed in body cleansing compositions.

Suitable anionic surfactants are, for example, alkyl sulfates, alkyl ether sulfates, alkyl sulfonates, alkylaryl sulfonates, alkyl succinates, alkyl sulfosuccinates, N-alkoylsarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium or calcium salts, and ammonium and triethanolamine salts, the alkyl ether sulfates, alkyl ether phosphates and alkyl ether carboxylates may have from 1 to 10 ethylene oxide or propylene oxide units, preferably from 1 to 3 ethylene oxide units, in the molecule.

These include, for example, sodium laurylsulfate, ammonium laurylsulfate, sodium lauryl ether sulfate, ammonium lauryl ether sulfate, sodium laurylsarcosinate, sodium oleylsuccinate, ammonium laurylsulfosuccinate, sodium dodecylbenzenesulfonate and triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates or alkyl amphodiacetates or -dipropionates.

For example, cocodimethylsulfopropylbetaine, laurylbetaine, cocamidopropylbetaine or sodium cocamphopropionate, may be used.

Examples of suitable nonionic surfactants are the reaction products of aliphatic alcohols or alkylphenols having 6 to 20 carbon atoms in the alkyl chain, which may be linear or branched, with ethylene oxide and/or propylene oxide. The amount of alkylene oxide is from about 6 to 60 moles per mole of alcohol. Furthermore, alkylamine oxides, mono- or dialkylalkanolamides, fatty esters of polyethylene glycols, ethoxylated fatty amides, alkylpolyglycosides or sorbitan ether esters are suitable.

The wash, shower and bath preparations may also comprise conventional cationic surfactants, such as quaternary ammonium compounds, for example cetyltrimethylammonium chloride.

The shower gel/shampoo formulations may furthermore comprise thickeners, e.g. sodium chloride, PEG-55, propylene glycol oleate, PEG-120-methylglucose dioleate and others, and preservatives, further active substances and excipients and water.

According to a particularly preferred embodiment, the novel compositions are a hair treatment composition.

Novel hair treatment compositions preferably comprise at least one novel copolymer in an amount of from about 0.1 to 30, preferably from 0.5 to 20, % by weight, based on the total weight of the composition.

The novel hair treatment compositions are preferably in the form of a hair setting foam, hair mousse, hair gel, shampoo, hair spray, hair foam, damaged end fluid, neutralizing composition for permanent waves, hair coloring and bleaching composition or hot oil treatment. Depending on the field of use, the cosmetic hair formulations may be applied as (aerosol) spray, (aerosol) foam, gel, gel spray, cream, lotion or wax. Hair sprays comprise both aerosol sprays and pump sprays without propellant. Hair foams comprise both aerosol foams and pump foams without propellant. Hair sprays and hair foams preferably comprise predominantly or exclusively water-soluble or water-dispersible components. If the compounds used in the novel hair sprays and hair foams are water-dispersible, they may be used in the form of aqueous microdispersions having particle diameters of, usually, from 1 to 350 nm, preferably from 1 to 250 nm. The solids contents of these preparations are usually from about 0.5 to 20% by weight. As a rule, these microdispersions require no emulsifiers or surfactants for their stabilization.

In a preferred embodiment, the novel cosmetic hair formulations comprise
a) from 0.05 to 20% by weight of at least one copolymer, as defined above,
b) from 20 to 99.95% by weight of water and/or alcohol,
c) from 0 to 50% by weight of at least one propellant,
d) from 0 to 5% by weight of at least one emulsifier,
e) from 0 to 3% by weight of at least one thickener and
f) up to 25% by weight of further components.

Alcohol is to be understood as meaning all alcohols customary in cosmetics, e.g. ethanol, isopropanol and n-propanol.

Further components are to be understood as meaning the additives customary in cosmetics, for example propellants, antifoams, surface-active compounds, i.e. surfactants, emulsifiers, foam formers and solubilizers. The surface-active compounds used may be anionic, cationic, amphoteric or neutral. Further conventional components may furthermore be, for example, preservatives, perfume oils, opacifiers, active substances, UV filters, care substances, such as panthenol, collagen, vitamins, protein hydrolysis products, alpha- and beta-hydroxycarboxylic acids, stabilizers, pH regulators, dyes, viscosity regulators, gel formers, salts, moisturizers, refatting agents, complexing agents and further conventional additives.

These furthermore include all styling and conditioner polymers which are known in cosmetics and can be used in combination with the novel polymers if it is intended to establish very specific properties.

For establishing very specific properties, the formulations may additionally comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino-functional silicone compounds, such as amodimethicone (CTFA).

The novel copolymers are particularly suitable as setting compositions in hairstyling formulations, in particular hair sprays (aerosol sprays and pump sprays without propellant) and hair foams (aerosol foams and pump foams without propellant).

In a preferred embodiment, spray formulations comprise
a) from 0.1 to 10% by weight of at least one copolymer, as defined above,
b) from 20 to 99.9% by weight of water and/or alcohol,
c) from 0 to 70% by weight of at least one propellant,
d) from 0 to 20% by weight of further components.

Propellants are the propellants usually used for hair sprays or aerosol foams. Mixtures of propane/butane, pentane, dimethyl ether, 1,1-difluoroethane (HFC-152 a), carbon dioxide, nitrogen or compressed air are preferred.

A formulation for aerosol hair foams which is preferred according to the invention comprises
a) from 0.1 to 10% by weight of at least one copolymer, as defined above,
b) from 55 to 99.8% by weight of water and/or alcohol,
c) from 5 to 20% by weight of a propellant,
d) from 0.1 to 5% by weight of an emulsifier,
e) from 0 to 10% by weight of further components.

Emulsifiers which may be used are all emulsifiers usually employed in hair foams. Suitable emulsifiers may be nonionic, cationic or anionic or amphoteric.

Examples of nonionic emulsifiers (INCI nomenclature) are laureths, e.g. laureth4; ceteths, e.g. cetheth-1, polyethylene glycol cetyl ether; cetearaths, e.g. ceteareth-25, polyglycol fatty acid glycerides, hydroxylated lecithin, lactyl esters of fatty acids, and alkylpolyglycosides.

Examples of cationic emulsifiers are cetyldimethyl-2-hydroxyethylammonium dihydrogen phosphate, cetyltrimonium chloride, cetyltrimonium bromide, cocotrimonium methylsulfate, quaternium-1 to x (INCI).

Anionic emulsifiers may be selected, for example, from the group consisting of the alkyl sulfates, alkyl ether sulfates, alkyl sulfonates, alkylaryl sulfonates, alkyl succinates, alkyl sulfosuccinates, N-alkoylsarcosinates, acryl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium and calcium salts, and ammonium and triethanolamine salts. The alkyl ether sulfates, alkyl ether phosphates and alkyl ether carboxylates may have from 1 to 10 ethylene oxide or propylene oxide units, preferably from 1 to 3 ethylene oxide units, in the molecule.

A formulation suitable according to the invention for styling gels may, for example, be composed of:
a) from 0.1 to 10% by weight of at least one copolymer, as defined above,
b) from 80 to 99.85% by weight of water and/or alcohol,
c) from 0 to 3, preferably from 0.05 to 2, % by weight of a gel former,
d) from 0 to 20% by weight of further components.

However, the use of gel formers may be advantageous for establishing specific rheological properties or other performance characteristics of the gels. Gel formers which may be used are all gel formers customary in cosmetics. These include slightly crosslinked polyacrylic acid, for example carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, polyquaternium-32 (and) liquid paraffin (INCI), sodium acrylate copolymer (and) liquid paraffin (and) PPG-1 trideceth-6, acrylamidopropyltrimonium chloride/acrylamide copolymers, steareth-10 allyl ether acrylate copolymers, polyquaternium-37 (and) liquid paraffin (and) PPG-1 trideceth-6, polyquaternium 37 (and) propylene glycol dicaprate dicaprylate (and) PPG-1 trideceth-6, polyquaternium-7, polyquaternium-44.

The novel copolymers can be used as conditioners in cosmetic formulations.

The novel copolymers, as defined above, can preferably be used as setting compositions and/or conditioners in shampoo formulations. Preferred shampoo formulations comprise
a) from 0.05 to 10% by weight of at least one copolymer, as defined above,
b) from 25 to 94.95% by weight of water,
c) from 5 to 50% by weight of surfactants,
c) from 0 to 5% by weight of a further conditioner,
d) from 0 to 10% by weight of further cosmetic components.

In the shampoo formulations, all anionic, neutral, amphoteric or cationic surfactants usually employed in shampoos can be used.

Suitable anionic surfactants are, for example, alkyl sulfates, alkyl ether sulfates, alkyl sulfonates, alkylaryl sulfonates, alkyl succinates, alkyl sulfosuccinates, N-alkoylsarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium and calcium salts, and ammonium and triethanolamine salts. The alkyl ether sulfates, alkyl ether phosphates and alkyl ether carboxylates may have from 1 to 10 ethylene oxide or propylene oxide units, preferably from 1 to 3 ethylene oxide units, in the molecule.

For example, sodium laurylsulfate, ammonium laurylsulfate, sodium lauryl ether sulfate, ammonium lauryl ether sulfate, sodium lauroylsarcosinates, sodium oleylsuccinate, ammonium laurylsulfosuccinate, sodium dodecylbenzenesulfonate and triethanolamine dodecylbenzenesulfonate are suitable.

Suitable amphoteric surfactants are, for example, alkylbetaines, alkylamidopropylbetaines, alkylsulfobetaines, alkyl glycinates, alkyl carboxyglycinates, alkyl amphotacetates or -propionates or alkyl amphodiacetates or -dipropionates.

For example, cocodimethylsulfopropylbetaine, laurylbetaine, cocoamidopropylbetaine or sodium cocamphopropionate may be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is from about 6 to 60 moles per mole of alcohol. Furthermore, alkylamine oxides, mono- or dialkylalkanolamides, fatty esters of polyethylene glycols, alkylpolyglycosides or sorbitan ether esters are suitable.

The shampoo formulations may also comprise conventional cationic surfactants, such as quaternary ammonium compounds, for example cetyltrimethylammonium chloride.

In the shampoo formulations, conventional conditioners can be used in combination with the novel copolymers for achieving specific effects. These include, for example, the abovementioned cationic polymers with the name polyquaternium according to INCI, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamide copolymers (polyquaternium-7). It is furthermore possible to use protein hydrolysis products, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and aminofunctional silicone compounds, such as amodimethicone (CTFA). Cationic guar derivatives, such as guarhydroxypropyltrimonium chloride (INCI), may furthermore be used.

The invention furthermore relates to the use of a copolymer, as defined above, as an excipient in pharmacy, preferably as or in coating material(s) for solid dosage forms, for modifying rheological properties, as surface-active compound, as or in adhesive(s) and as or in coating material(s) for the textile, paper, printing and leather industry.

The nonlimiting examples which follow illustrate the invention.

EXAMPLES

General Preparation Method: Solution Polymerization in Ethanol/water (2:1)

Example 15

600 g of a 30% strength polymer solution (TBA/MAM/NtBAM/MAA=63:10:10:17)

Feed 1: Monomer mixture comprising:

| | |
|---|---|
| 113.4 g | of tert-butyl acrylate |
| 120 g | of methacrylamide (15% strength) |
| 18 g | of N-tert-butylacrylamide |
| 30.6 g | of acrylic acid |
| 147 g | of ethanol |

Feed 2: Initiator solution comprising:

| | |
|---|---|
| 0.5 g | of Wako ® 50 [2,2'-azobis(2-amindinopropane) dihydrochloride] |
| 21 g | of water |

Feed 3: Initiator solution comprising:

| | |
|---|---|
| 0.9 g | of 75% strength tert-butyl perpivalate |
| 42 g | of ethanol |

Feed 4: Neutralizing composition:

| | |
|---|---|
| 34 g | of 2-amino-2-methyl-propanol (AMP) |
| 97 g | of ethanol/water |

21 g of feed 1, 1 g of feed 2 and 108 g of ethanolwater (3.5:1) were initially taken in a stirred apparatus having a reflux condenser, internal thermometer and four separate feed apparatuses, and the mixture was heated to about 65° C. with stirring. After the prepolymerization, detectable by a slight increase in viscosity, the remainder of feed 1 was added at 67° C. in the course of three hours and the remainder of feed 2 in the course of four hours. The reaction solution was stirred for about a further two hours at 70° C. and then feed 3 was metered in in the course of 30 minutes at 70° C. After the addition, polymerization was effected for about another two hours at 80° C. Feed 4 was then metered in in the course of 10 minutes for neutralization. An aqueous/ethanolic solution of about 30% strength was obtained.

Polymers No. 1-44 were prepared analogously.

TABLE 1

| Ex. No. | TBA | TMBA | MAM | NtBAM | ACMO | VP | DMAA | AA | MAA | NtBAEMA | VI | DMAPMAM | Amine/N.G. [%] |
|---|---|---|---|---|---|---|---|---|---|---|---|---|---|
| 1 | 80 | — | 10 | — | — | — | — | 10 | — | — | — | — | AMP/95 |
| 2 | 75 | — | 15 | — | — | — | — | 10 | — | — | — | — | AMP/95 |
| 3 | 75 | — | 10 | — | — | — | — | 15 | — | — | — | — | AMP/90 |
| 4 | 73 | — | 10 | — | — | — | — | 17 | — | — | — | — | AMP/90 |
| 5 | 70 | — | 10 | — | — | — | — | 15 | 5 | — | — | — | AMP/85 |
| 6 | 70 | — | 10 | — | — | — | — | 20 | — | — | — | — | AMP/85 |
| 7 | 70 | — | 10 | — | — | — | — | 12 | 8 | — | — | — | AMP/85 |
| 8 | 70 | — | 10 | — | — | — | — | 10 | 10 | — | — | — | AMP/90 |
| 9 | 70 | — | 10 | — | — | — | — | 8 | 12 | — | — | — | AMP/95 |
| 10 | 65 | — | 15 | — | — | — | — | 10 | 10 | — | — | — | AMP/85 |
| 11 | 65 | — | — | 15 | — | — | — | 10 | 10 | — | — | — | AMP/85 |
| 12 | 65 | — | — | — | 15 | — | — | 10 | 10 | — | — | — | AMP/85 |
| 13 | 60 | — | — | 20 | — | — | — | 8 | 12 | — | — | — | AMP/95 |
| 14 | 60 | — | 10 | — | — | — | — | 8 | 22 | — | — | — | AMP/80 |
| 15 | 63 | — | 10 | 10 | — | — | — | 17 | — | — | — | — | AMP/90 |
| 16 | 60 | — | 15 | 10 | — | — | — | 15 | — | — | — | — | AMP/95 |
| 17 | 60 | — | 10 | 15 | — | — | — | 15 | — | — | — | — | AMP/95 |
| 18 | 55 | — | 10 | 20 | — | — | — | 15 | — | — | — | — | AMP/95 |
| 19 | 55 | — | 10 | 15 | — | — | — | 20 | — | — | — | — | AMP/85 |
| 20 | 50 | — | 13 | 20 | — | — | — | 17 | — | — | — | — | AMP/90 |
| 21 | 50 | — | 15 | — | — | 20 | — | 15 | — | — | — | — | AMP/80 |
| 22 | 50 | — | — | 15 | — | 20 | — | 15 | — | — | — | — | AMP/80 |
| 23 | 63 | 10 | 10 | — | — | — | — | 17 | — | — | — | — | AMP/95 |
| 24 | 63 | 10 | — | 10 | — | — | — | 17 | — | — | — | — | AMP/95 |
| 25 | 40 | 20 | — | 25 | — | — | — | 15 | — | — | — | — | AMP/95 |
| 26 | 55 | — | 20 | — | — | — | — | 15 | 10 | — | — | — | AMP/85 |
| 27 | 55 | — | — | 20 | — | — | — | 15 | 10 | — | — | — | AMP/85 |
| 28 | 55 | — | — | — | 20 | — | — | 15 | 10 | — | — | — | AMP/85 |
| 29 | 55 | — | — | — | — | 20 | — | 15 | 10 | — | — | — | AMP/85 |
| 30 | 70 | — | 5 | — | — | — | — | 20 | — | 5 | — | — | AMP/85 |
| 31 | 65 | — | 10 | — | — | — | — | 20 | — | 5 | — | — | AMP/85 |
| 32 | 65 | — | 15 | — | — | — | — | 15 | — | — | 5 | — | AMP/85 |
| 33 | 65 | — | 15 | — | — | — | — | 17 | — | — | — | 3 | AMP/85 |
| 34 | 60 | — | 10 | — | — | — | — | 10 | 12 | 8 | — | — | AMP/95 |
| 35 | 60 | — | 10 | — | — | — | — | 25 | — | — | 5 | — | AMP/90 |
| 36 | 60 | — | — | 12 | — | — | — | 22 | — | 6 | — | — | AMP/90 |
| 37 | 55 | — | — | 20 | — | — | — | 8 | 12 | 5 | — | — | AMP/95 |
| 38 | 30 | 30 | — | 12 | — | — | — | 22 | — | — | — | 6 | AMP/95 |
| 39 | 40 | — | 10 | — | — | 25 | — | 15 | — | 10 | — | — | AMP/85 |

TABLE 2

| Ex. No. | TBA | EMA | MAM | NtBAM | AA | MAA |
|---|---|---|---|---|---|---|
| 40 | 65 | — | — | 10 | 5 | 20 |
| 41 | 40 | 25 | 15 | — | 8 | 12 |
| 42 | 48 | 20 | — | 7 | 5 | 20 |
| 43 | 40 | 25 | — | 10 | 8 | 17 |
| 44 | 35 | 27 | — | 15 | 3 | 20 |

TBA: tert-butyl acrylate
TBMA: tert-butyl methacrylate
EMA: ethyl methacrylate
MAM: methacrylamide
NtBAM: N-tert-butylacrylamide
ACMO: acryloylmorpholine
VP: vinylpyrrolidone
DMAA: N,N-dimethylacrylamide
AA: acrylic acid
MAA: methacrylic acid
NtBAEMA: N-tert-butylaminoethyl methacrylate
VI: vinylimidazole
DMAPMAM: dimethylaminopropylmethacrylamide
AMP: 2-amino-2-methylpropanol
N.G.: degree of neutralization Use examples:
I) Use in hair cosmetics:
1) VOC 80 aerosol hair spray (examples No. 1-39)

| | |
|---|---|
| Polymers 1-39 (30% strength aqueous ethanolic solution) | 10.0 |
| Water | 14.6 |
| Dimethyl ether | 40.0 |
| Ethanol | 35.4 |
| Further additives: | |
| Preservative, soluble ethoxylated silicone, perfume, antifoam . . . | |

2) VOC 80 aerosol hair spray (examples No. 40-78)

| | |
|---|---|
| Polymers 1-39 (30% strength aqueous ethanolic solution) | 6.6 |
| Luvimer ® 100P | 1.0 (TBA/EA/MAA terpolymer, from BASF) |
| Water | 15.5 |
| Dimethyl ether | 40.0 |
| Ethanol | 37.0 |
| Further additives: | |
| Preservative, soluble ethoxylated silicone, perfume, antifoam . . . | |

3) VOC 55 aerosol hair spray (examples No. 79-122)

| | |
|---|---|
| Polymers 1-44 (30% strength aqueous ethanolic solution) | 10.0 |
| Water | 39.6 |
| Dimethyl ether | 40.0 |
| Ethanol | 10.4 |
| Further additives: | |
| Preservative, soluble ethoxylated silicone, perfume, antifoam . . . | |

4) VOC 55 aerosol hair spray (examples No. 123-166)

| | |
|---|---|
| Polymers 1-44 (30% strength aqueous ethanolic solution) | 10.0 |
| Luviset ® PUR (30% strength solution) | 5.0 (polyurethane, from BASF) |
| Water | 35.1 |
| Dimethyl ether | 40.0 |
| Ethanol | 9.9 |
| Further additives: | |
| Preservative, soluble ethoxylated silicone, perfume, antifoam . . . | |

5) VOC 55 pump spray (examples No. 167-210)

| | |
|---|---|
| Polymers 1-44 (30% strength aqueous ethanolic solution) | 13.5 |
| Water | 37.8 |
| Ethanol | 48.7 |
| Further additives: | |
| Preservative, soluble ethoxylated silicone, perfume, antifoam . . . | |

6) Foam setting composition (examples No. 211-234)

| | |
|---|---|
| Polymer No. 6, 10, 12, 14, 21, 22, 26, 28, 29, 30, 31, 32, 33, 34, 35, 36, 37, 38, 39, 40, 41, 42, 43, 44 (30% strength solution) | 10.0 |
| Cremophor ® A 25 | 0.2 (ceteareth 25, from BASF) |
| Comperlan ® KD | 0.1 (coamide DEA, from Henkel) |
| Water | 79.7 |
| Dimethyl ether | 10.0 |

Further additives: Perfume, preservative . . .
Preparation: Weigh in, and dissolve with stirring. Fill, and add propellant.

7) Foam setting composition (examples No. 235-258)

| | |
|---|---|
| Polymer No. 6, 10, 12, 14, 21, 22, 26, 28, 29, 30, 31, 32, 33, 34, 35, 36, 37, 38, 39, 40, 41, 42, 43, 44 (30% strength solution) | 10.0 |
| Luviflex ® Soft (10% strength aqueous solution, pH = 7) | 15.0 (acrylate copolymer, from BASF) |
| Cremophor ® A 25 | 0.2 (ceteareth 25, from BASF) |
| Comperlan ® KD | 0.1 (coamide DEA, from Henkel) |
| Water | 64.7 |
| Dimethyl ether | 10.0 |

Further additives: Perfume, preservative . . .
Preparation: Weigh in, and dissolve with stirring. Fill, and add propellant.

8) Hair gel (examples No. 259-282)

| | [%] |
|---|---|
| Phase 1: | |
| Polymer No. 6, 10, 12, 14, 21, 22, 26, 28, 29, 30, 31, 32, 33, 34, 35, 36, 37, 38, 39, 40, 41, 42, 43, 44 (30% strength solution) | 10.0 |
| Distilled water | 39.0 |
| Aminomethylpropanol (38% strength solution) | 1.0 |
| Further additives: Preservative, soluble ethoxylated silicone, perfume . . . | |
| Phase 2: | |
| Acrylic acid/beheneth-25 methacrylate copolymer (Aculyn ® 28 from Rohm und Haas, 1% strength aqueous suspension) | 50.0 |

Preparation: The components of phases 1 and 2 are weighed in separately and homogenized. Phase 2 is slowly stirred into phase 1. A clear, viscous gel forms.

9) Hair gel (examples No. 283-306)

| | [%] |
|---|---|
| Phase 1: | |
| Polymer No. 6, 10, 12, 14, 21, 22, 26, 28, 29, 30, 31, 32, 33, 34, 35, 36, 37, 38, 39, 40, 41, 42, 43, 44 (30% strength solution) | 10.0 |
| Distilled water | 40.0 |
| Further additives: Preservative, soluble ethoxylated silicone, perfume . . . | |
| Phase 2: | |
| Hydroxyethylcellulose (Natrosol ® HR 250, from Hercules 5% strength aqueous solution) | 50.0 |

Preparation: The components of phases 1 and 2 are weighed in separately and homogenized. Phase 1 is slowly stirred into phase 2. A clear, pourable gel forms.

II) Use in skin cosmetics:

10) Standard OAN cream (examples No. 307-322)

| | % | CTFA name |
|---|---|---|
| Oil phase: | | |
| Cremophor A6 | 3.5 | Ceteareth-6 (and) Stearyl Alcohol |
| Cremophor A25 | 3.5 | Ceteareth-25 |
| Glyceryl monostearate s.e. | 2.5 | Glyceryl Stearate |
| Liquid paraffin | 7.5 | Paraffin Oil |
| Cetyl alcohol | 2.5 | Cetyl Alcohol |
| Luvitol EHO | 3.2 | Cetearyl Octanoate |
| Vitamin E acetate | 1.0 | Tocopheryl Acetate |
| Nip-nip | 0.1 | Methyl and propyl-4-hydroxybenzoate (7:3) |
| Aqueous phase: | | |
| Polymer No. 21, 30, 31, 32, 33, 34, 35, 36, 37, 38, 39, 40, 41, 42, 43, 44 (20% strength aqueous solution) | 3.0 | |
| Water | 74.6 | |
| 1,2-Propylene glycol | 1.5 | Propylene Glycol |
| Germall II | 0.1 | Imidazolidinyl-Urea |

Preparation: The components are weighed in and the oil phase and aqueous phase are homogenized separately at about 80° C. with stirring. The aqueous phase is slowly stirred into the oil phase and the mixture is cooled to room temperature with stirring.

We claim:

1. A hairspray composition comprising
   A) at least one copolymer obtained by free radical polymerization of a monomer mixture consisting of:
      a) tert-butyl acrylate,
      b) methacrylamide and/or N-(tert-butyl)acrylamide,
      c) acrylic acid,
      d) optionally, methacrylic acid, and
      e) optionally, N-(tert-butyl)aminoethyl (meth)acrylate or N-[3-(dimethylamino)-propyl]methacrylamide or N-vinylimidazole, and
   B) at least one cosmetically or pharmaceutically acceptable carrier.

2. The hairspray composition according to claim 1, wherein component b) is methacrylamide.

3. The hairspray composition according to claim 1, wherein component b) is N-(tert-butyl)acrylamide.

4. The hairspray composition according to claim 1, wherein the monomer mixture comprises methacrylic acid as component d).

5. The hairspray composition according to claim 1, wherein the monomer mixture contains N-(tert-butyl)aminoethyl (meth)acrylate or N-[3-(dimethylamino)propyl]methacrylamide or N-vinylimidazole.

6. The hairspray composition according to claim 1, wherein the component B) is selected from
   i) water,
   ii) water-miscible organic solvents,
   iii) oils, fats, waxes,
   iv) esters of $C_6$-$C_{30}$-monocarboxylic acids with monohydric, dihydric or trihydric alcohols, which esters differ from 11i),
   v) saturated acyclic and cyclic hydrocarbons,
   vi) fatty acids,
   vii) fatty alcohols,
   viii) propellants
   and mixtures thereof.

7. The hairspray composition according to claim 1, comprising at least one additive which differs from the components A) and B) and is selected from the group consisting of cosmetically active substances, emulsifiers, surfactants, preservatives, perfume oils, thickeners, hair polymers, hair and skin conditioners, graft polymers, water-soluble or dispersible silicone-containing polymers, light stabilizers, bleaches, gel formers, care compositions, colorants, tinting compositions, tanning compositions, dyes, pigments, consistency agents, humidifiers, refatting agents, collagen, protein hydrolysis products, lipids, antioxidants, antifoams, antistatic agents, emollients and softeners.

8. The hairspray composition according to claim 1, wherein the composition is a hair setting composition and/or a conditioner.

* * * * *